(12) United States Patent
Maeda et al.

(10) Patent No.: US 9,517,109 B2
(45) Date of Patent: Dec. 13, 2016

(54) MEDICAL SYSTEM

(71) Applicant: OLYMPUS CORPORATION, Hachioji-shi, Tokyo (JP)

(72) Inventors: Yorito Maeda, Kiyose (JP); Kuniaki Kami, Hachioji (JP); Koichi Tashiro, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/202,967

(22) Filed: Jul. 6, 2016

(65) Prior Publication Data

US 2016/0310228 A1 Oct. 27, 2016

Related U.S. Application Data

(63) Continuation of application No. PCT/JP2015/058326, filed on Mar. 19, 2015.

(30) Foreign Application Priority Data

Sep. 24, 2014 (JP) .................................. 2014-194294

(51) Int. Cl.
*G06T 7/00* (2006.01)
*G06K 9/00* (2006.01)
(Continued)

(52) U.S. Cl.
CPC ........... *A61B 90/37* (2016.02); *G02B 27/2292* (2013.01); *G03H 1/0248* (2013.01); *G03H 1/08* (2013.01);
(Continued)

(58) Field of Classification Search
CPC ... A61B 90/37; A61B 2090/373; G06T 7/004; G06T 7/0012; G06T 2207/30004; G06K 9/00228; G06K 9/00355; G06K 9/00375; H04N 7/183; G02B 27/2292; G03H 1/0248; G03H 1/08; G03H 1/0866; G03H 2001/0038

See application file for complete search history.

(56) References Cited

U.S. PATENT DOCUMENTS 8,704,822 B2 * 4/2014 Butler ................ G02B 27/2292
345/419
9,161,817 B2 * 10/2015 Olson .................... A61B 5/042
(Continued)

FOREIGN PATENT DOCUMENTS

JP  H07-231896 A  9/1995
JP  2001-142027 A  5/2001
(Continued)

OTHER PUBLICATIONS

Machine translation of JP 2001-142027.*
Machine translation of JP 2009-100996.*
(Continued)

*Primary Examiner* — Katrina Fujita
(74) *Attorney, Agent, or Firm* — Oliff PLC

(57) ABSTRACT

A medical system that is capable of displaying a virtual image, comprising: a sensor comprising hardware, wherein the sensor implements: a first detection section that detects information related to at least one of a position and an orientation of an operator; a second detection section that detects a position of an object in a surgery room; and a processor comprising hardware, wherein the processor implements: a calculation section that calculates an area where the virtual image is to be arranged in the air based on the information; a determination section that determines whether or not the object is present in the area based on a result of the detection by the second detection section; and (Continued)

a control section that causes the virtual image to be arranged in the area based on a determination result by the determination section.

10 Claims, 9 Drawing Sheets

(51) Int. Cl.
    *H04N 7/18* (2006.01)
    *G02B 27/22* (2006.01)
    *G03H 1/08* (2006.01)
    *G03H 1/02* (2006.01)
    *G03H 1/00* (2006.01)

(52) U.S. Cl.
    CPC ........ *G03H 1/0866* (2013.01); *G06K 9/00228* (2013.01); *G06K 9/00355* (2013.01); *G06K 9/00375* (2013.01); *G06T 7/004* (2013.01); *G06T 7/0012* (2013.01); *H04N 7/183* (2013.01); *A61B 2090/373* (2016.02); *G03H 2001/0038* (2013.01); *G06T 2207/30004* (2013.01)

(56) References Cited

U.S. PATENT DOCUMENTS

| | | | |
|---|---|---|---|
| 9,241,768 B2 * | 1/2016 | Sandhu | A61B 19/2203 |
| 9,439,736 B2 * | 9/2016 | Olson | A61B 34/25 |
| 2005/0025706 A1 | 2/2005 | Kagermeier | |
| 2005/0128184 A1 * | 6/2005 | McGreevy | A61B 18/1206 345/156 |
| 2008/0013793 A1 * | 1/2008 | Hillis | G03H 1/0005 382/114 |
| 2009/0237759 A1 * | 9/2009 | Maschke | A61B 6/037 359/9 |
| 2010/0020926 A1 * | 1/2010 | Boese | A61B 5/06 378/44 |
| 2011/0128555 A1 | 6/2011 | Rotschild et al. | |
| 2013/0225999 A1 * | 8/2013 | Banjanin | A61B 8/467 600/443 |
| 2014/0282008 A1 * | 9/2014 | Verard | G03H 1/00 715/728 |
| 2015/0250450 A1 * | 9/2015 | Thomas | A61B 8/4416 600/411 |

FOREIGN PATENT DOCUMENTS

| | | |
|---|---|---|
| JP | 2005-040613 A | 2/2005 |
| JP | 2009-100996 A | 5/2009 |
| JP | 2011-527760 A | 11/2011 |
| JP | 2014-067071 A | 4/2014 |
| JP | 2014-139621 A | 7/2014 |
| JP | 2014-153602 A | 8/2014 |
| WO | 2009/131128 A1 | 10/2009 |

OTHER PUBLICATIONS

Liao et al. "3D Medical Imaging and Augmented Reality for Image-Guided Surgery", 2011, 3D Medical Imaging and Augmented Reality for Image-Guided Surgery, 589-602.*
Jun. 16, 2015 Search Report issued in International Patent Application No. PCT/JP2015/058326.
Apr. 5, 2016 Decision to Grant a Patent issued in Japanese Patent Application No. 2016-504244.

* cited by examiner

MEDICAL SYSTEM

CROSS REFERENCE TO RELATED APPLICATION

This application is a continuation application of PCT/JP2015/058326 filed on Mar. 19, 2015 and claims benefit of Japanese Application No. 2014-194294 filed in Japan on Sep. 24, 2014, the entire contents of which are incorporated herein by this reference.

BACKGROUND OF THE INVENTION

1. Field of the Invention

The present invention relates to a medical system, and more particularly to a medical system capable of displaying a virtual display screen in the air.

2. Description of the Related Art

In recent years, with the development in technology, more varieties of medical devices have appeared, and functions of the medical devices have been enhanced. In addition to such medical devices, various kinds of equipment such as room lights, various kinds of display apparatuses, an endoscope that picks up a medical image, a recording apparatus, and the like are arranged in a surgery room.

Furthermore, Japanese Patent Application Laid-Open Publication No. 7-231896 discloses an endoscopic surgery system including a centralized control apparatus (system controller) that performs centralized control of various kinds of medical devices including the above-described apparatuses by communication.

In the centralized control apparatus in the endoscopic surgery system of this type, it is common to set or change parameters, etc., of devices to be controlled by using an operation panel configured by what is called a touch panel, and it is desirable that the operation of the operation panel is performed by a surgeon by himself or herself who is in a sterilized area.

As disclosed in Japanese Patent Application Laid-Open Publication No. 2005-040613, a gesture apparatus is known as an input apparatus that can be used also in the sterilized area. In addition, in recent years, a technology of displaying a display as a virtual image in the air is proposed in WO 2009/131128.

Combination of the technology disclosed in the above-described Japanese Patent Application Laid-Open Publication No. 2005-040613 and the technology (technology of showing a virtual display in the air) disclosed in WO 2009/131128 allows a virtual aerial display having a GUI function which is almost the same as that of a touch panel to be shown in a predetermined spatial position in a surgery room.

The virtual aerial display provided with the GUI (graphical user interface) function does not require a physical contact with the input operation screen due to the principle thereof, that is, the principle that the aerial display is a virtual image shown in a space. Therefore, implementation of such showing of the aerial display enables the surgeon to perform input operation also in the sterilized area.

Furthermore, the aerial display is shown at an arbitrary timing, thereby capable of preventing the field of view from being interfered with the operation panel.

SUMMARY OF THE INVENTION

A medical system according to one aspect of the present invention is a medical system that is capable of displaying a virtual image, comprising: a sensor comprising hardware, wherein the sensor implements: a first detection section that detects information related to at least one of a position and an orientation of an operator; a second detection section that detects a position of an object in a surgery room; and a processor comprising hardware, wherein the processor implements: a calculation section that calculates an area where the virtual image is to be arranged in the air based on the information; a determination section that determines whether or not the object is present in the area based on a result of the detection by the second detection section; and a control section that causes the virtual image to be arranged in the area based on a determination result by the determination section.

DETAILED DESCRIPTION OF THE PREFERRED EMBODIMENTS

Hereinafter, embodiments of the present invention will be described with reference to drawings.

First Embodiment

Figure 1:
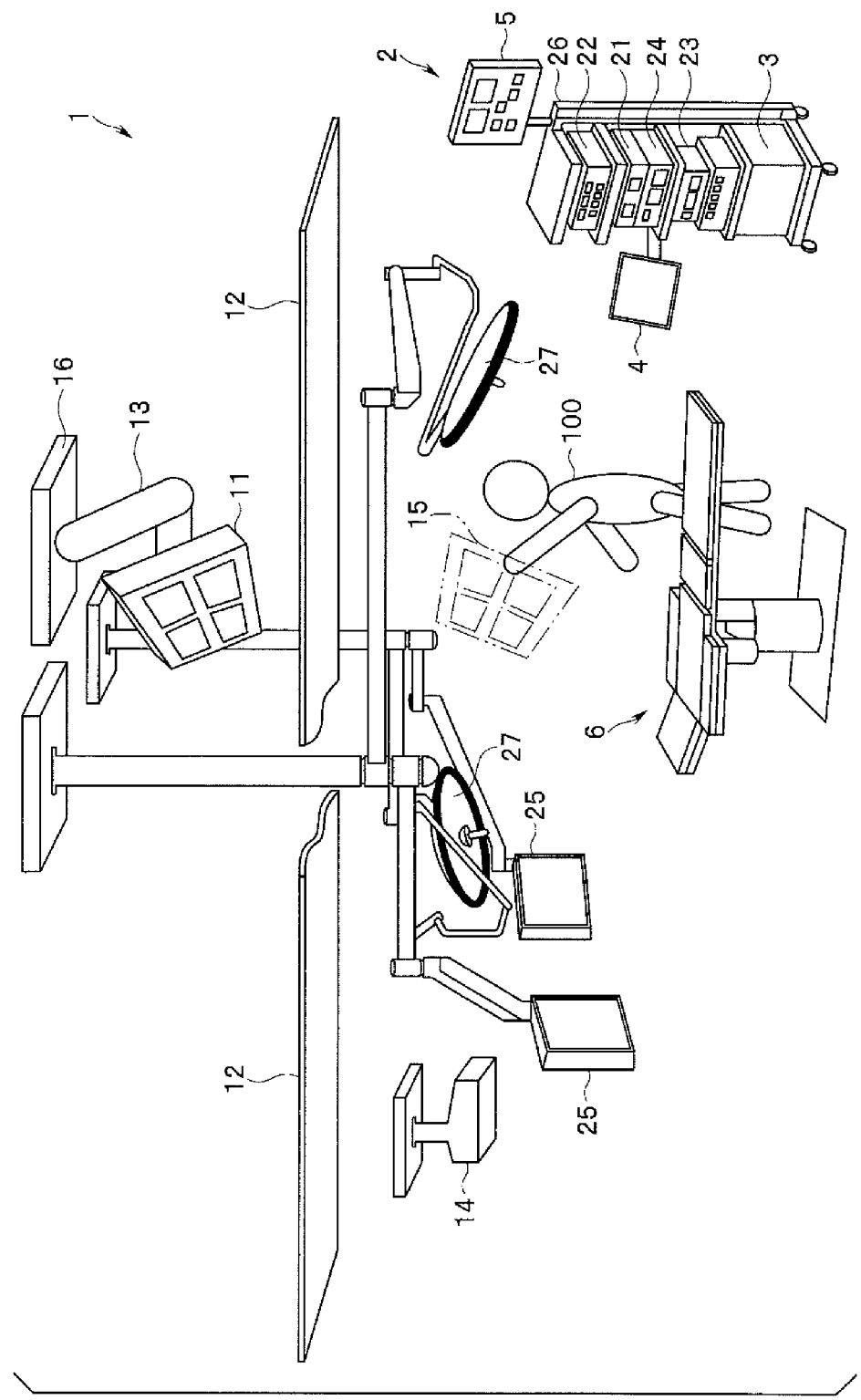
FIG. 1 illustrates an overall configuration of a medical system according to a first embodiment of the present invention.
Figure 2:
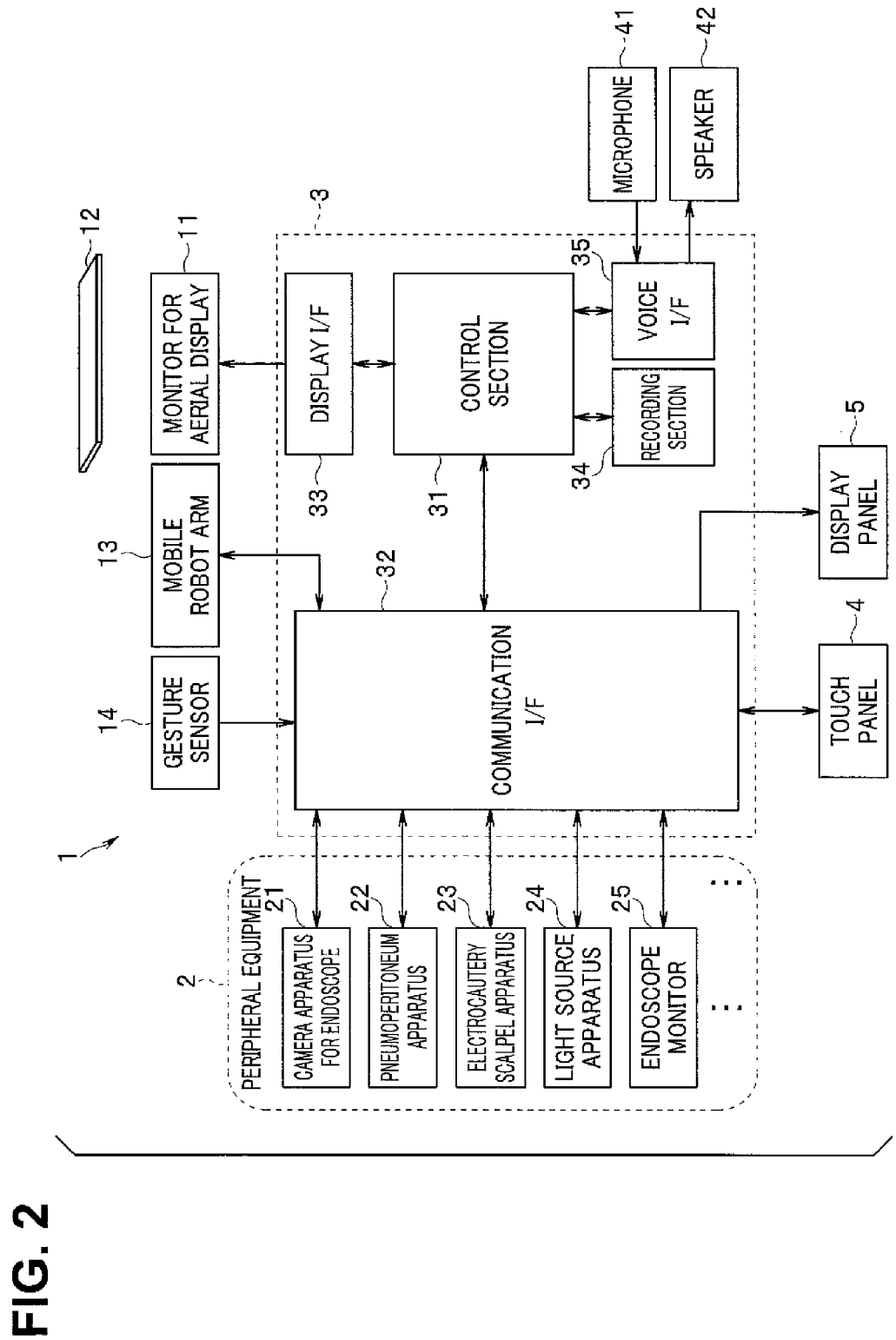
FIG. 2 illustrates an electric configuration of the medical system according to the first embodiment.
Figure 3:
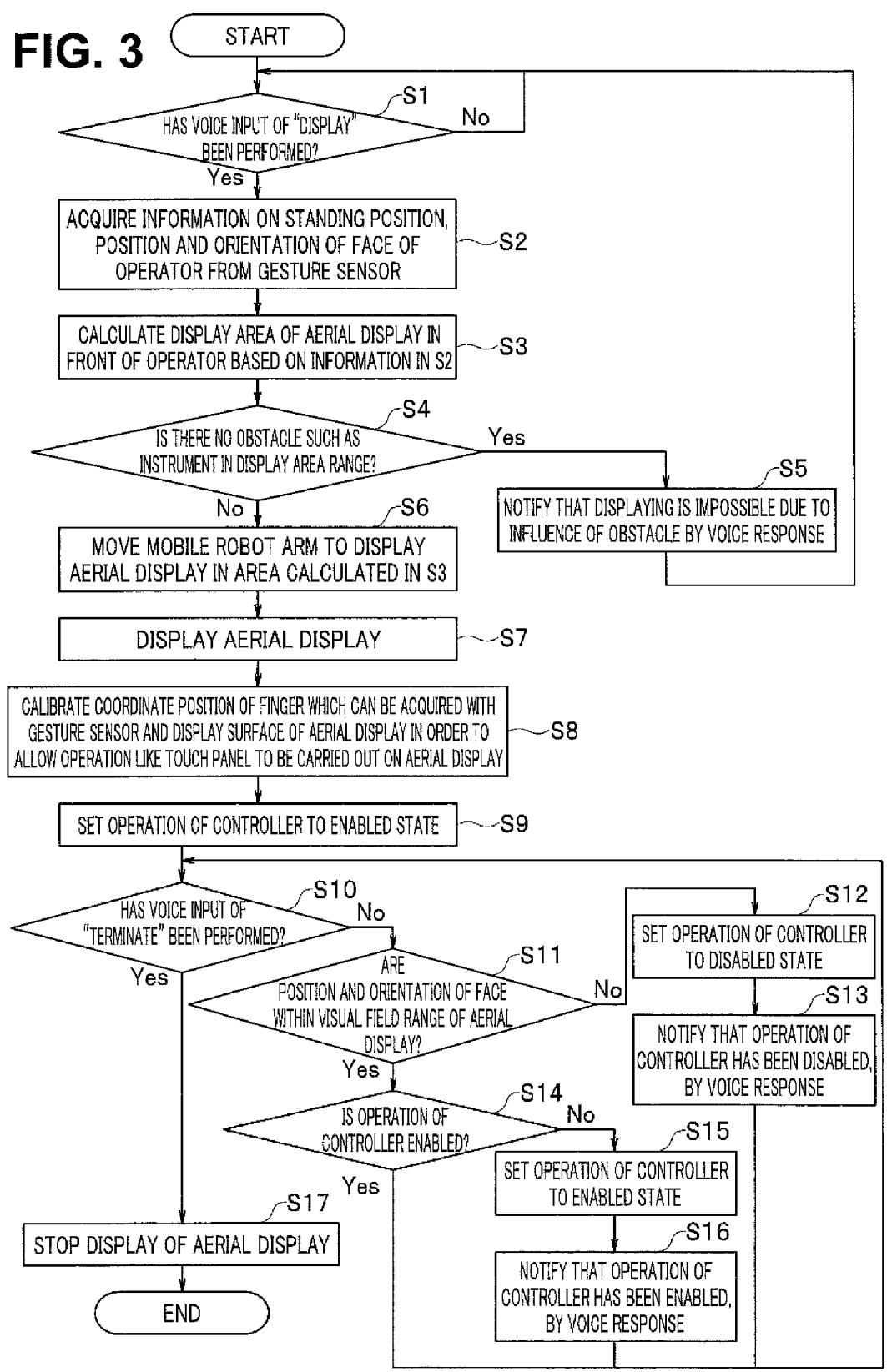
FIG. 3 is a flowchart showing a control action of an aerial display in the medical system according to the first embodiment.
Figure 4:
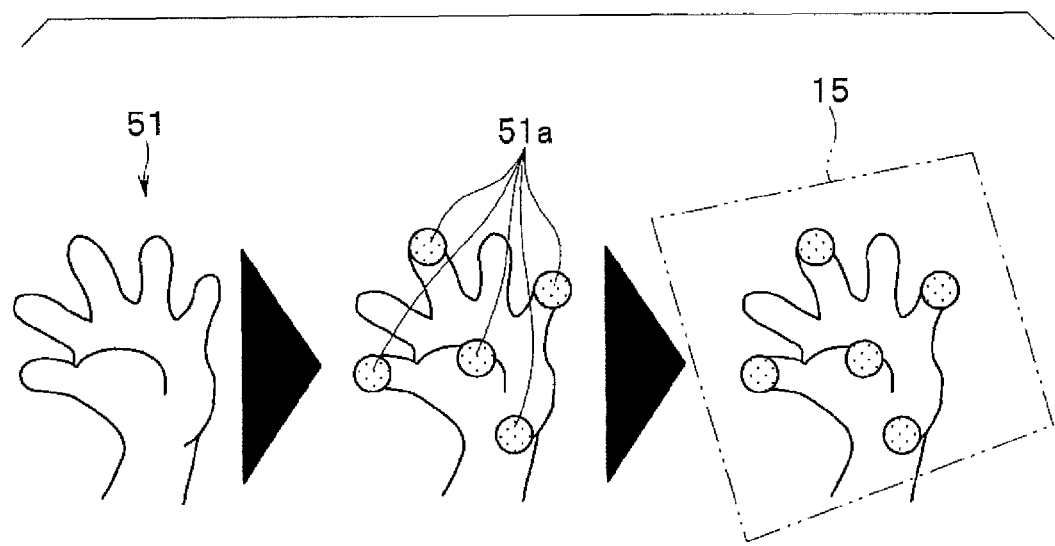
FIG. 4 illustrates a detection operation of position information on hand and fingers of an operator in the medical system according to the first embodiment.

With reference to FIGS. 1 to 4, a medical system according to the first embodiment will be described. FIG. 1 illustrates an overall configuration of the medical system according to the first embodiment of the present invention, FIG. 2 illustrates an electric configuration of the medical system according to the first embodiment, FIG. 3 is a flowchart showing a control action of an aerial display in the medical system according to the first embodiment, and FIG. 4 illustrates a detection operation of position information on the hand and fingers of an operator in the medical system according to the first embodiment.

As shown in FIG. 1, a medical system 1 according to the present embodiment is a system placed in a surgery room where endoscopic surgery is performed, and as shown in FIG. 1 and FIG. 2, the main part of the medical system 1 is configured by including: a peripheral equipment group 2 as devices to be controlled constituted of a plurality of medical devices; a system controller 3 that performs centralized control of the peripheral equipment group 2 and controls various kinds of devices; an operation panel 4 that accepts an operation performed by an operator such as a nurse; a display panel 5 that selectively displays predetermined information related to a surgery; a surgical bed 6 on which a patient lies; a monitor for aerial display 11 on which an original image for a virtual aerial display 15 including an input operation function (GUI function) is displayed; a plate for aerial display 12 for displaying the virtual aerial display; a mobile robot arm 13 that changes the position and orientation of the monitor for aerial display 11; a gesture sensor 14 that recognizes the devices and the like in the surgery room and a gesture of a predetermined part of the surgeon (operator) 100; a microphone 41 that collects voice of the surgeon and the like; and a speaker 42 for emitting predetermined voice to the surgeon and the like.

The peripheral equipment group 2 is configured by a plurality of medical devices that perform observation, examination, treatment and the like. In the medical system according to the present embodiment, the plurality of medical devices, for example, include: a camera apparatus for endoscope 21, an insufflation apparatus 22, an electrocautery scalpel apparatus 23, a light source apparatus 24, an endoscope monitor 25, and the like. Note that the peripheral equipment group 2 is not limited to these medical devices and may include a video tape recorder (VTR) and the like, for example.

The system controller 3 controls the peripheral equipment group 2 and various kinds of apparatuses in the medical system 1, and as shown in FIG. 2, the main part of the system controller is configured by a control section 31 that performs various kinds of control, a communication I/F 32 which is an interface for communication signals for communicating with the operation panel 4, the display panel 5, the mobile robot arm 13, the gesture sensor 14, etc. as well as with the peripheral equipment group 2, a display I/F 33 connected with the monitor for aerial display 11, a recording section 34 that records predetermined information, and a voice I/F 35 connected with the microphone 41 and the speaker 42.

The control section 31 in the system controller 3 acts as: a calculation section that calculates a first area in which the virtual aerial display 15 is arranged based on information related to at least one of the position and direction of the surgeon, as the operator of the virtual aerial display 15, in the surgery room; a determination section that determines whether or not a predetermined object is present in the first area; and a control section that controls the monitor for aerial display 11, the mobile robot arm 13, etc., so as to arrange the virtual aerial display 15 in the first area when the determination section determines that the object does not present in the first area.

The communication I/F 32 is an interface for receiving various kinds of data, setting parameters, and the like from the peripheral equipment group 2 connected to the system controller 3, inputting these data, parameters, and the like to the control section 31, or outputting the signal for operating the peripheral equipment group 2, which has been generated in the control section 31, to the peripheral equipment group 2. In addition, the recording section 34 stores a program for activating the system controller 3 and various kinds of data, parameters, etc., required for executing the program, for example.

Note that detailed description will be made later on the control to be performed by the system controller 3 with respect to the monitor for aerial display 11, the mobile robot arm 13, the gesture sensor 14, the microphone 41, and the speaker 42.

The operation panel 4 is configured by what is called a touch panel display which includes, in an integrated manner, a liquid crystal display and a touch panel sensor arranged stacked on the liquid crystal display, for example. The operation panel 4 is an operation apparatus used by the nurse or the like who is in unsterilized area for operating the peripheral equipment group 2, and the operational information is inputted to the control section 31 through the communication I/F 32 in the system controller 3.

The light source apparatus 24 is connected to an endoscope (not shown) through a light guide cable that transmits illumination light. The illumination light from the light source apparatus 24 is supplied to the endoscope, to illuminate a diseased part and the like in the abdomen of the patient into which the insertion portion of the endoscope is inserted.

In the medical system according to the present embodiment, a camera head including an image pickup device is mounted on the proximal end side of the insertion portion of the endoscope, to pick up an optical image such as the diseased part with the image pickup device in the camera head. The image pickup signal obtained by the image pickup device is transmitted to the camera apparatus for endoscope 21 through a cable.

The camera apparatus for endoscope 21 performs predetermined signal processing on the image pickup signal transmitted from the endoscope connected thereto, to generate a video signal. Then, the camera apparatus for endoscope 21 outputs the generated video signal to the monitor 25 through the system controller 3. Note that, in the present embodiment, the monitor 25 is suspended from a ceiling 16 so as to be movable, and displays the inputted video signal, that is, an endoscopic image of the diseased part, and the like.

The insufflation apparatus 22 is connected with a carbon dioxide bottle, not shown, and configured to supply carbon dioxide into the abdomen of the patient through an insufflation tube extended from the insufflation apparatus 22 to the patient.

In addition to the system controller 3, the operation panel 4, the display panel 5, the camera apparatus for endoscope 21, the insufflation apparatus 22, the electrocautery scalpel apparatus 23, and the light source apparatus 24 are arranged on a rack 26.

Note that the system controller 3 also controls the facilities permanently disposed in the surgery room such as the surgical bed 6 on which the patient lies, a shadowless lamp 27 suspended from the ceiling 16, as the devices to be controlled, in addition to the above-described peripheral equipment group 2.

In addition, the medical system 1 provided in the surgery room where endoscopic surgery is performed is shown as an example in FIG. 1. However, the intended purpose of the medical system 1 is not limited to the endoscopic surgery, and may be used for other surgeries or medical examinations. Furthermore, the medical system 1 may be provided in an examination room other than the surgery room.

The medical system 1 may further include various kinds of apparatuses and facilities which are not shown in FIG. 1. For example, the medical system 1 may include a surgical field camera for observing the surgical field, and the like, and the surgical field camera and the like may be controlled by the system controller 3.

Next, description will be made on the virtual aerial display including an input operation function (GUI function) which characterizes the present invention and a display mechanism of the aerial display, with reference to FIG. 1 and FIG. 2.

The monitor for aerial display 11 is a monitor that displays an original image for the virtual aerial display 15 (see FIG. 1) including the input operation function (GUI function), and disposed from the ceiling 16 through the mobile robot arm 13, as shown in FIG. 1.

The "original image" for the virtual aerial display 15, which is displayed on the monitor for aerial display 11, is controlled by the control section 31 in the system controller 3 through the display I/F 33. Note that the "original image" is an operation panel screen which is like the one displayed on the operation panel 4 which is a touch panel.

The mobile robot arm 13 is extended from the ceiling 16 and supports the monitor for aerial display 11 so as to be movable with respect to the ceiling 16. The mobile robot arm 13 is connected to the control section 31 through the communication I/F 32, and controls the position and the orientation of the display surface of the monitor for aerial display 11 under the control by the control section 31.

The plate for aerial display 12 is a plate having a function for displaying the video displayed on the monitor for aerial display 11 as the virtual aerial display 15, and disposed so as to be fixed at a predetermined position substantially below the monitor for aerial display 11 in the surgery room where the medical system 1 is disposed.

The plate for aerial display 12 includes a function for displaying the virtual aerial display in the space in the surgery room as disclosed in the re-publication of PCT International Publication No. 2009-131128.

Then, a light beam from the display surface of the monitor for aerial display 11 is image-formed in the air in a position symmetrical to the display surface of the monitor for aerial display 11, with the plate for aerial display 12 as a plane of symmetry, and the video displayed on the monitor for aerial display 11 is shown as a virtual image (virtual aerial display 15) in the air.

The gesture sensor 14 is a detection sensor which is disposed at a predetermined position in the surgery room, and which recognizes the gesture of a predetermined part of the operator such as a surgeon who operates the virtual aerial display 15, to thereby detect information on the position or orientation of the predetermined part in the surgery room.

In the present embodiment, the gesture sensor 14 is configured to detect not only the position and direction information on the standing position, the position of the face, the orientation (direction) of the face of the surgeon (operator) in the surgery room but also the positions of the hand and fingers of the surgeon as shown in FIG. 4.

Furthermore, the gesture sensor 14 is capable of detecting not only the position and direction information related to the surgeon (operator) but also the position information on the devices arranged in the surgery room (the peripheral equipment group 2, the operation panels 4, 5, and also arbitrarily arranged devices, instruments, or the like in the surgery room).

That is, the gesture sensor 14 serves as a first detection section that detects information on at least one of the position and direction of the operator and a second detection section that detects an object present in a first area where the display is to be arranged based on the information.

The microphone 41 is a microphone that collects the voice of the surgeon and the like, and configured to collect the voice for controlling the action of the system controller 3 with respect to the control section 31 that controls the monitor for aerial display 11 in the present embodiment. Furthermore, the speaker 42 is a speaker for emitting predetermined voice to the surgeon and the like, and has a function for emitting predetermined warning voice when the system controller 3 controls the monitor for aerial display 11 in the present embodiment.

<Position Control of Aerial Display>

Next, description will be made on how to perform the position control of the virtual aerial display 15 shown in the space in the surgery room in the medical system 1 according to the present embodiment.

As described above, the virtual aerial display 15 has a narrow viewing angle, and the operator (surgeon) cannot visually recognize the virtual aerial display unless he or she stands in front of the display surface. However, in a surgery scene, the standing position of the surgeon is limited in many cases, and the surgeon cannot necessarily be positioned always at the same position and in the same orientation. That is, it is considered to be difficult for the surgeon to stand in front of the display surface of the aerial display all the time with ease.

The present invention has been made in view of the above-described circumstances, and the gesture sensor 14 is provided at a predetermined position in the surgery room in the present embodiment, as described above. The gesture sensor 14 detects the information on the standing position, the position of the face, and the orientation (direction) of the face of the surgeon (operator) in the surgery room, to send the position and direction information to the system controller 3.

The control section 31 in the system controller 3 that acquires the position and direction information drives the mobile robot arm 13, to move the monitor for aerial display 11 such that the virtual aerial display 15 is positioned in front of the operator.

After the monitor for aerial display 11 is moved to an accurate position under the control by the system controller 3, the virtual aerial display 15 can be shown in a position which is plane-symmetrical to the display surface of the monitor for aerial display 11 with respect to the plate for aerial display 12. That is, the virtual aerial display 15 is shown in the position in front of the operator in the space of the surgery room.

In the present embodiment, the virtual aerial display 15 moved to the position in front of the operator is further finely adjusted according to the coordinate positions of the hand and fingers of the operator. That is, calibration of the coordinate positions of the hand and fingers of the operator and the display surface of the virtual aerial display 15 is possible.

In the present embodiment, the gesture sensor 14 is configured to detect the positions of the hand and fingers of the surgeon (operator) as shown in FIG. 4, as described above. Specifically, the gesture sensor 14 detects the coordinate positions of predetermined feature points 51a on the palm 51 of the operator and sends the position information to the system controller 3.

After acquiring the coordinate position information of the feature points 51a on the palm 51 of the operator from the gesture sensor 14, the system controller 3 drives and controls the mobile robot arm 13, to adjust the position and the orientation of the monitor for aerial display 11 such that the coordinate positions of the hand and fingers of the operator match with the display surface of the virtual aerial display 15.

This adjustment allows the calibration of the coordinate positions of the hand and fingers of the operator and the display surface of the virtual aerial display 15. In the present embodiment, the gesture sensor 14 detects the coordinate positions of the feature points 51a on the palm 51 of the operator as needed and the system controller 3 adjusts the position of the monitor for aerial display 11 as needed, which enables the calibration to be executed continuously.

As described above, in the state where the calibration of the coordinate positions of the hand and fingers of the operator and the display surface of the virtual aerial display 15 is executed continuously, the hand and fingers of the operator are arranged superimposed on the operation image of the virtual aerial display 15, for example, and the gesture sensor 14 detects the coordinate positions of the feature points 51a on the palm 51 which are the hand and fingers of the operator, to thereby enable the operator to operate the operation panel screen (GUI screen) displayed on the display surface of the virtual aerial display 15 shown in the space in the surgery room as if the operation panel screen were a touch panel present at the site. That is, the virtual aerial display 15 is provided with the input operation function (GUI function).

Working of First Embodiment

Next, description will be made on the working of the medical system according to the first embodiment of the present invention.

FIG. 3 is a flowchart showing a control action of the aerial display in the medical system according to the first embodiment.

As shown in FIG. 3, when receiving a voice input of "display" inputted through the microphone 41 by a surgeon (operator) 100 (step S1), the control section 31 in the system controller 3 acquires the position and direction information related to the standing position and the position or orientation (direction) of the face of the operator 100 in the surgery room which has been detected by the gesture sensor 14 (step S2).

Then, the control section 31 calculates an area where the virtual aerial display 15 is located right in front of the operator 100, based on the position and direction information related to the operator 100 which has been acquired in the step S2 (step S3).

Furthermore, based on the information from the gesture sensor 14, the control section 31 determines whether or not any obstacle such as a device, instrument or the like is present in an area where the virtual aerial display 15 is to be shown in the surgery room (step S4).

When an obstacle is present in the step S4, the control section 31 controls the speaker 42 to output voice for notifying that the virtual aerial display 15 cannot be shown due to the effect of the obstacle (step S5).

When the control section 31 determines that no obstacle is present in the area where the virtual aerial display 15 is to be shown in step S4, the control section 31 drives and controls the mobile robot arm 13 based on the position and direction information related to the operator 100, which has been acquired in step S2, to move the monitor for aerial display 11 such that the virtual aerial display 15 is positioned in front of the operator (step S6).

After the monitor for aerial display 11 is moved to an accurate position under the control by (the control section 31) in the system controller 3 in step S6, the virtual aerial display 15 is shown in the position which is plane-symmetrical to the display surface of the monitor for aerial display 11 with respect to the plate for aerial display 12 (step S7).

The control section 31 calibrates the coordinate positions of the hand and fingers of the operator and the display surface of the virtual aerial display 15 (step S8). That is, as described above, in the medical system according to the present embodiment, the gesture sensor 14 first detects the coordinate positions of the predetermined feature points 51a on the palm 51 of the operator, to send the position information to the system controller 3 (see FIG. 4).

Then, the control section 31 acquires the coordinate position information of the feature points 51a on the palm 51 of the operator from the gesture sensor 14, drives and controls the mobile robot arm 13, and performs calibration by adjusting the position and orientation of the monitor for aerial display 11 such that the coordinate positions of the hand and fingers of the operator match with the display surface of the virtual aerial display 15.

In the present embodiment, as described above, the calibration of the coordinate positions of the hand and fingers of the operator and the display surface of the virtual aerial display 15 is continuously executed, which enables the operator to operate the operation panel screen (GUI screen) displayed on the display surface of the virtual aerial display 15 shown in the space in the surgery room as if the operation panel screen were the touch panel present at the site.

In the state where the calibration of the coordinate positions of the hand and fingers of the operator and the display surface of the virtual aerial display 15 is continuously executed, the control section 31 enables "operation of controller" which allows the GUI screen on the virtual aerial display 15 to be operated like the touch panel (step S9).

Note that, in the present embodiment, when the "operation of controller" is enabled and the operation of the GUI screen on the virtual aerial display 15 becomes available, the surgeon (operator) can operate the various kinds of devices such as the peripheral equipment group 2 in the sterilized area, for example.

After "operation of controller" is brought into the enabled state in step S9 until the control section 31 receives a voice input of "terminate" from the surgeon (operator) 100 (step S10), the control section 31 monitors the position of the face of the operator 100 based on the information from the gesture sensor 14, to determine whether or not the position and orientation of the face of the operator 100 is positioned within a visual field range of the virtual aerial display 15 (step S11).

That is, the surgeon (operator) sometimes moves in the surgery room depending on the procedure of the operation, but due to the narrow visual field range of the virtual aerial display 15, as described above, if the operator 100 moves, the operator 100 cannot visually confirm the virtual aerial display 15. If, in this state, the "operation of controller" related to the virtual aerial display 15 remains enabled, the hand or the like of the operator 100 erroneously enters the display range of the virtually image aerial display 15, which is likely to lead malfunction of the peripheral equipment group 2, etc.

In view of the above-described points, in the present invention, after the "operation of controller" is enabled, the position and orientation of the face of the operator 100 is monitored to prevent an unexpected accident. That is, in step S11, when the control section 31 determines that the position of the face of the operator 100 has deviated from the visual field range of the virtual aerial display 15, the control section 31 disables the "operation of controller" (step S12). That is, the control section 31 disables the GUI operation related to the virtual aerial display 15 which functions like the touch panel floating in the space.

In addition, the control section 31 drives the speaker 42, to notify the operator 100 that the "operation of controller" has been disabled, by voice response (step S13).

As long as the position of the face of the operator 100 is within the visual field range of the virtual aerial display 15 in step S11, the control section 31 continues the enabled state of the "operation of controller" (step S14). In the case where the position of the face of the operator 100 is positioned again within the visual field range of the virtual aerial display 15 after the "operation of controller" was disabled once in the step S12, the control section 31 sets the "operation of controller" to enabled state again (step S15), and notifies the operator 100 that the "operation of controller" has been enabled, by voice response (step S16).

When receiving the voice input of "terminate" from the operator 100 in the state where the "operation of controller" is enabled in step S10, the control section 31 stops the screen display on the monitor for aerial display 11, which results in disappearance of the virtual aerial display 15 which was being shown in the space until then (step S17).

As described above, according to the medical system of the first embodiment, the virtual aerial display provided with the input operation function (GUI function) like the touch panel can be shown in an accurate spatial position in the surgery room.

This enables the surgeon who is in the sterilized area to operate the various kinds of peripheral equipment in the medical system as if he or she operates the touch panel without touching the apparatuses located in the unclean area.

Furthermore, according to the first embodiment, in addition to the above-described effects, when the virtual aerial display provided with the input operation function like the touch panel as described above is shown in a predetermined spatial position, the monitor for aerial display 11 and the like are controlled such that the virtual aerial display is shown after confirming the presence or absence of an obstacle in advance. Therefore, it is possible to prevent malfunction to be caused by unintended movement of the hand and fingers of the operator or the devices which are already present in the surgery room.

Furthermore, according to the first embodiment, in addition to the above-described effects, even after the virtual aerial display provided with the input operation function like the touch panel as described above is shown in the predetermined spatial position, the position information of the operator is monitored, to thereby prevent malfunction to be caused by unintended movement of the hand and fingers of the operator even in the case where the operator is deviated from the visual field range of the virtual aerial display.

Second Embodiment

Next, description will be made on the second embodiment of the present invention.

In the medical system according to the above-described first embodiment, when showing the virtual aerial display provided with the input operation function like the touch panel as described above in the predetermined spatial position, the control section 31 in the system controller 3 recognizes the voice input of "display" from the surgeon (operator) (step S1 in FIG. 3), and thereafter acquires the position and direction information related to the standing position, and the position or orientation (direction) of the face of the operator in the surgery room with the gesture sensor 14 (step S2 in FIG. 3). Then, the control section 31 calculates the position where the virtual aerial display 15 is located right in front of the operator, based on the position and direction information related to the operator (step S3 in FIG. 3), to thereby determine whether or not any obstacle such as a device, instrument or the like is present in the area in the surgery room where the virtual aerial display 15 is to be shown (step S4 in FIG. 3), and control the monitor for aerial display 11 and the like such that the virtual aerial display 15 is shown after confirming the presence or absence of the obstacle (step S5 in FIG. 3).

The medical system according to the second embodiment is the same as the one in the first embodiment in that when the virtual aerial display provided with the input operation function like the touch panel as described above is shown in the predetermined spatial position, the control section 31 starts activation of the showing system of the virtual aerial display by recognizing the voice input of "display" from the operator. The medical system according to the second embodiment, however, is characterized in that, after the activation of the showing system, the control section 31 acquires position and direction information related to the position or direction of the "palm" of the operator 100 with the gesture sensor 14, and based on the position and direction information of the "palm", calculates the position of the virtual aerial display 15 in accordance with the surface of the "palm", and then similarly as in the first embodiment, the control section 31 controls the monitor for aerial display 11 and the like after confirming the presence or absence of an obstacle in an area where the virtual aerial display 15 is to be displayed.

That is, the medical system according to the second embodiment has a basic configuration similar to that of the medical system according to the first embodiment, but a part of the control action of the aerial display is different from that in the first embodiment. Therefore, hereinafter, only the points different from the first embodiment will be described and description on the parts same as those in the first embodiment will be omitted.

Working of Second Embodiment

Hereinafter, description will be made on the working of the medical system according to the second embodiment of the present invention.

Figure 5:
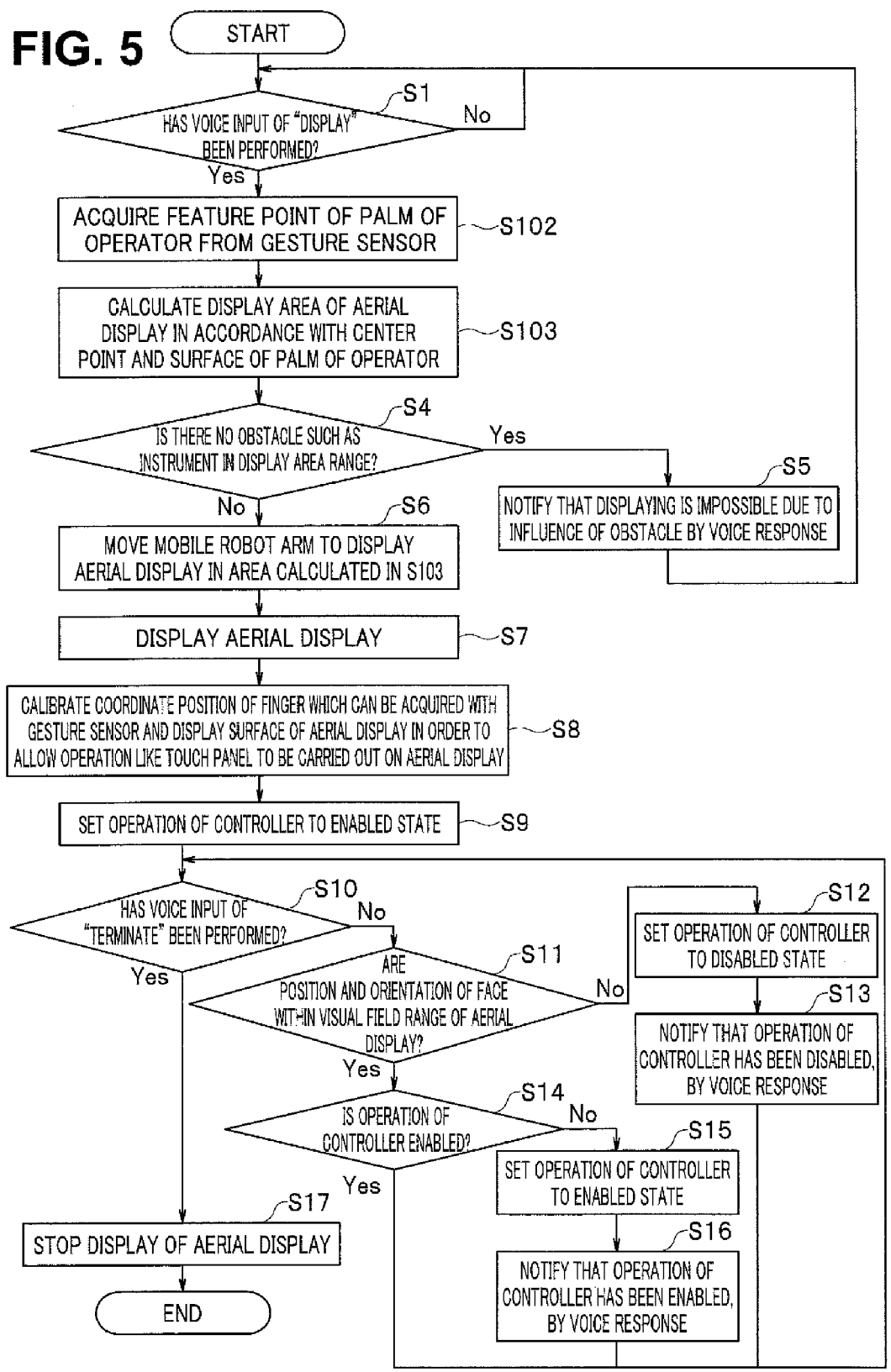
FIG. 5 is a flowchart showing a control action of an aerial display in a medical system according to a second embodiment of the present invention.

FIG. 5 is a flowchart showing the control action of the aerial display in the medical system according to the second embodiment of the present invention.

As shown in FIG. 5, in the second embodiment, when receiving voice input of "display" inputted through the microphone 41 by the surgeon (operator) 100 (step S1), the control section 31 in the system controller 3 acquires the feature points of the "palm" of the operator 100 in the surgery room based on the position information from the gesture sensor 14 (step S102).

That is, the control section 31 performs control such that the gesture sensor 14 detects the coordinate positions of predetermined feature points 51a on the palm 51 of the operator (see FIG. 4) and the detected position information is transmitted to the system controller 3.

After that, the control section 31 acquires, from the gesture sensor 14, the coordinate position information of the feature points 51a on the palm 51 of the operator, and calculates the showing position of the virtual aerial display 15 in accordance with the position of the "palm" (that is, in accordance with the center point of the palm and the surface of the palm), based on the coordinate position information of the "palm" (step S103).

After that, the control section 31 determines whether or not any obstacle such as a device, instrument, or the like is present in the area where the virtual aerial display 15 is to be displayed, the area having been calculated in the step S103 (step S4).

When an obstacle is present in the step S4, similarly as in the first embodiment, the control section 31 controls the speaker 42 to output voice notifying that the virtual aerial display 15 cannot be shown due to the effect of the obstacle (step S5).

When determining that no obstacle is present in the area where the virtual aerial display 15 is to be shown in step S4, the control section 31 drives and controls the mobile robot arm 13, to move the monitor for aerial display 11 such that the virtual aerial display 15 is shown in the area calculated in the step S103 (step S6).

After the monitor for aerial display 11 is moved to an accurate position under the control by (the control section 31) in the system controller 3 in the step S6, the virtual aerial display 15 is shown in the position which is plane-symmetrical to the display surface of the monitor for aerial display 11 with respect to the plate for aerial display 12 (step S7).

After that, similarly as in the first embodiment, the control section 31 calibrates the coordinate positions of the hand and fingers of the operator and the display surface of the virtual aerial display 15 (step S8), and in the state where the calibration of the coordinate positions of the hand and fingers of the operator and the display surface of the virtual aerial display 15 is continuously executed, the control section 31 enables "operation of controller" which allows the GUI screen on the virtual aerial display 15 to be operated like the touch panel (step S9).

The "operation of controller" is the same as that in the above-described first embodiment, description thereof will be omitted below.

As described above, similarly as in the first embodiment, the medical system according to the second embodiment is capable of showing the virtual aerial display provided with the input operation function (GUI function) like a touch panel in an accurate spatial position in the surgery room, thereby enabling the surgeon who is in the sterilized area to operate the various kinds of peripheral equipment in the medical system as if he or she operates the touch panel without touching the apparatuses in the unclean area.

Further, according to the second embodiment, when the virtual aerial display provided with the input operation function like the touch panel as described above is shown in the predetermined spatial position, the monitor for aerial display 11 is controlled such that the virtual aerial display is shown after confirming the presence or absence of an obstacle in advance, thereby capable of preventing malfunction to be caused by the devices and the like which are already disposed in the surgery room.

Furthermore, according to the second embodiment, even after the virtual aerial display provided with the input operation function like the touch panel as described above is shown in the predetermined spatial position, the position information of the operator is monitored, to thereby prevent malfunction to be caused by unintended movement of the hand and fingers of the operator even in the case where the operator is deviated from the visual field range of the virtual aerial display.

In addition, according to the second embodiment, the virtual aerial display 15 is shown in the position over which the operator holds up his or her "palm". That is, the virtual aerial display 15 can be displayed at such a position that the operator's intention is more properly reflected.

Third Embodiment

Next, description will be made on the third embodiment of the present invention.

In the medical system according to the above-described first embodiment, the monitor for aerial display 11, which is used for showing the virtual aerial display provided with the input operation function like the touch panel as described above in the predetermined spatial position, is configured to be movable through the mobile robot arm 13. Such a configuration enables also the position in the surgery room where the virtual aerial display 15 is shown to be set with a relatively high degree of freedom.

In contrast, the medical system according to the third embodiment is characterized to have a simple configuration in which the monitor for aerial display is fixed to a predetermined position in the surgery room, though the showing position of the virtual aerial display is limited to a relatively restricted position.

In addition, since the position of the monitor for aerial display is fixed, a size-reduced plate is used as the above-described plate for aerial display.

Thus, the showing position of the virtual aerial display in the medical system according to the third embodiment is limited compared to the first embodiment. The medical system according to the third embodiment, however, can omit the moving mechanism and control mechanism for the monitor for aerial display, and has an advantage that the virtual aerial display can be shown in the surgery room with a smaller-scale system.

Figure 6:
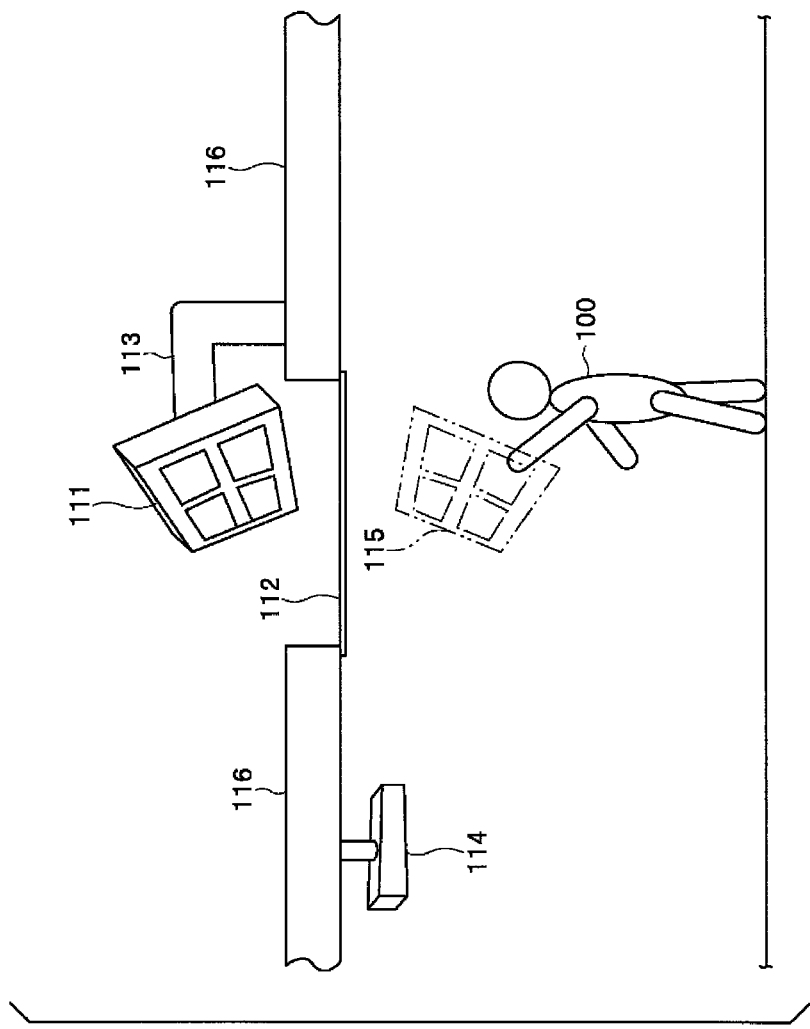
FIG. 6 illustrates a configuration of a main part of a medical system according to a third embodiment of the present invention.
Figure 7:
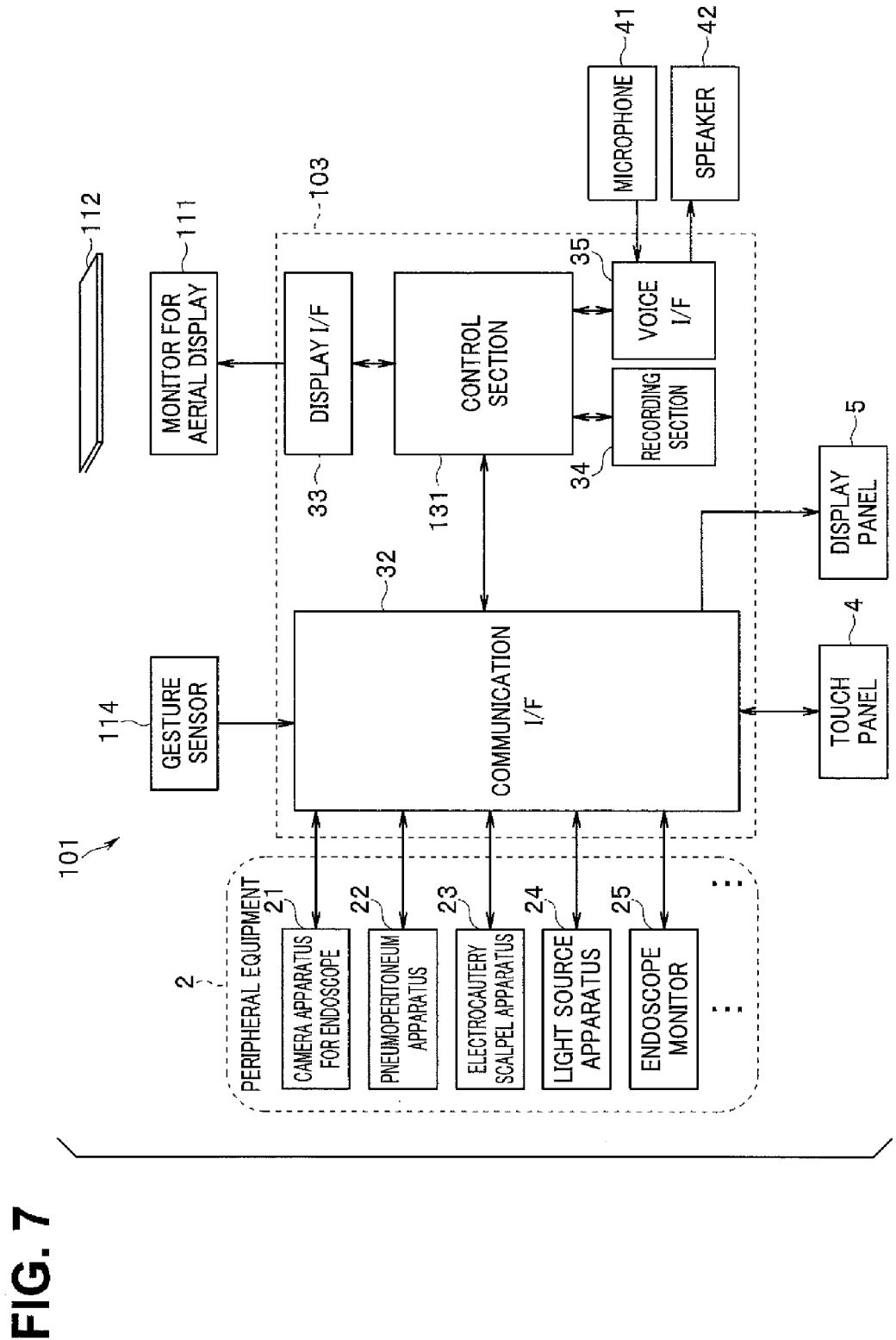
FIG. 7 illustrates an electric configuration of the medical system according to the third embodiment.

FIG. 6 illustrates the main part of the medical system according to the third embodiment of the present invention, and shows the configuration of the main part of the mechanism related to the showing of the virtual aerial display, and FIG. 7 illustrates an electrical configuration in the medical system according to the third embodiment.

As shown in FIG. 6 and FIG. 7, a medical system 101 according to the third embodiment is a system provided in the surgery room where an endoscopic surgery is performed, and the main part of the system is configured by including: a peripheral equipment group 2 as devices to be controlled which are constituted of a plurality of medical devices similar to as those in the first embodiment; a system controller 103 that performs centralized control of the peripheral equipment group 2 and controls various kinds of devices; an operation panel 4 that accepts an operation performed by an operator such as a nurse; a display panel 5 as a display section that selectively displays predetermined information related to a surgery; a surgical bed 6 on which a patient lies (not shown in FIG. 6); a monitor for aerial display 111 that displays an original image for a virtual aerial display 115 provided with an input operation function (GUI function); a plate for aerial display 112 for displaying the virtual aerial display; an arm 113 that fixedly supports the monitor for aerial display 111 at a predetermined position in the surgery room; a gesture sensor 114 that recognizes the devices, etc., in the surgery room and a gesture of a predetermined part of the surgeon (operator) 100; a microphone 41 that collects voice of the surgeon and the like; and a speaker 42 for emitting predetermined voice to the surgeon and the like.

That is, the medical system according to the third embodiment is different from the one in the first embodiment in the moving mechanism and the control mechanism for the monitor for aerial display which is used for showing the virtual aerial display, but other configurations are the same as those in the first embodiment. Hereinafter, description will be made just on the parts different from those in the first embodiment and description on the parts same as those in the first embodiment will be omitted.

In the third embodiment, the system controller 103 controls the peripheral equipment group 2 and various apparatuses in the medical system 101, and as shown in FIG. 7, has a main part configured by a control section 131 that performs various kinds of control, a communication I/F 32 which is an interface for communication signals for communicating with the operation panel 4, the display panel 5, the mobile robot arm 13, the gesture sensor 114, etc., as well as with the peripheral equipment group 2, a display I/F 33 connected with the monitor for aerial display 111, the recording section 34 that records predetermined information, and the voice I/F 35 connected with the microphone 41 and the speaker 42.

Next, description will be made on the virtual aerial display according to the third embodiment and the display mechanism of the aerial display, with reference to FIG. 6 and FIG. 7.

In the third embodiment, the monitor for aerial display 111 is a monitor for displaying an original image for the virtual aerial display 115 provided with the input operation function (GUI function), and disposed supported with the arm 113 at a top surface portion of a ceiling 116 (above-ceiling portion) in the surgery room where the medical system 101 is disposed, as shown in FIG. 6.

The "original image" for the virtual aerial display 115, which is displayed on the monitor for aerial display 111, is controlled by the control section 131 in the system controller 103 through the display I/F 33, similarly as in the first embodiment.

The plate for aerial display 112 is a plate provided with a function same as that of the plate for aerial display 12 in the first embodiment, that is, a plate having a function for displaying a video displayed on the monitor for aerial display 111 as the virtual aerial display 115.

In addition, the plate for aerial display 112 is disposed at a cut-out part of the ceiling 116 which is cut out such that the surgery room is viewed from above, so as to block the cut-out part and to be positioned in the direction substantially parallel to the extending surface of the ceiling 116. Note that, since the function of the plate for aerial display 112 is same as that of the plate for aerial display 12 in the first embodiment, description thereof will be omitted.

Furthermore, the monitor for aerial display 111 is disposed such that the display surface is arranged in the position facing the plate for aerial display 112, which is exposed at the cut-out part of the ceiling 116, from the back side of the ceiling 116.

According to such a configuration, in the third embodiment, a light beam from the display surface of the monitor for aerial display 111 is image-formed in the air in the position symmetrical to the display surface of the monitor for aerial display 111, with the plate for aerial display 112 as a symmetrical surface, and the video displayed on the monitor for aerial display 111 is shown as the virtual image (virtual aerial display 115) in the air in the surgery room.

Since the virtual aerial display as described above is a virtual image, the viewing angle (visual field range) is narrow. Therefore, the operator (surgeon) cannot visually recognize the virtual aerial display unless the operator (surgeon) stands in front of the display surface. In the present third embodiment, since the monitor for aerial display 111 is fixed, the showing position of the virtual aerial display 115 is limited.

In view of such circumstances, the medical system according to the third embodiment is characterized to grasp the positional relationship between the current standing position of the operator and the showing position of the virtual aerial display 115, and provide predetermined information to the operator so as to guide the operator into the visual field range of the virtual aerial display 115 when the standing position of the operator is deviated from the visual field range of the virtual aerial display 115.

Referring back to FIG. 6, the gesture sensor 114 is a detection sensor which is disposed at the predetermined position in the surgery room and which recognizes the gesture of the predetermined part of the operator, such as a surgeon, who operates the virtual aerial display 115, to thereby detect information on the position or orientation of the predetermined part of the operator in the surgery room, similarly as in the first embodiment.

Furthermore, in the third embodiment, the gesture sensor 114 detects not only the positions of the hand and fingers of the surgeon (operator) as shown in FIG. 4, but also the information and the like of the standing position of the operator in the surgery room, to send the position information to the system controller 103.

Specifically, in the third embodiment, the system controller 103 that acquires the position information from the gesture sensor 114 is configured to detect the hand gesture motion of the operator by detecting the coordinate positions of the predetermined feature points 51a on the palm 51 of the operator (see FIG. 4).

In addition, the system controller 103 is configured to acquire the information on the standing position of the operator in the surgery room from the gesture sensor 114 and calculate the distance between the standing position of the operator and the visual field range of the virtual aerial display 115.

Then, the system controller 103 activates the monitor for aerial display 111 to show the virtual aerial display 115 in the air when the current standing position of the operator 100 is within the visual field range of the virtual aerial display 115.

When the standing position of the operator 100 is outside the visual field range of the virtual aerial display 115, the system controller 103 performs control to display the information indicating the positional relationship between the standing position of the operator 100 and the visual field range of the virtual aerial display 115 on the operation panel 4, and also controls the speaker 42 to provide the information on the distance to the virtual aerial display 115 to the operator 100 by voice response.

Working of Third Embodiment

Next, description will be made on the working of the medical system according to the third embodiment of the present invention.

Figure 8:
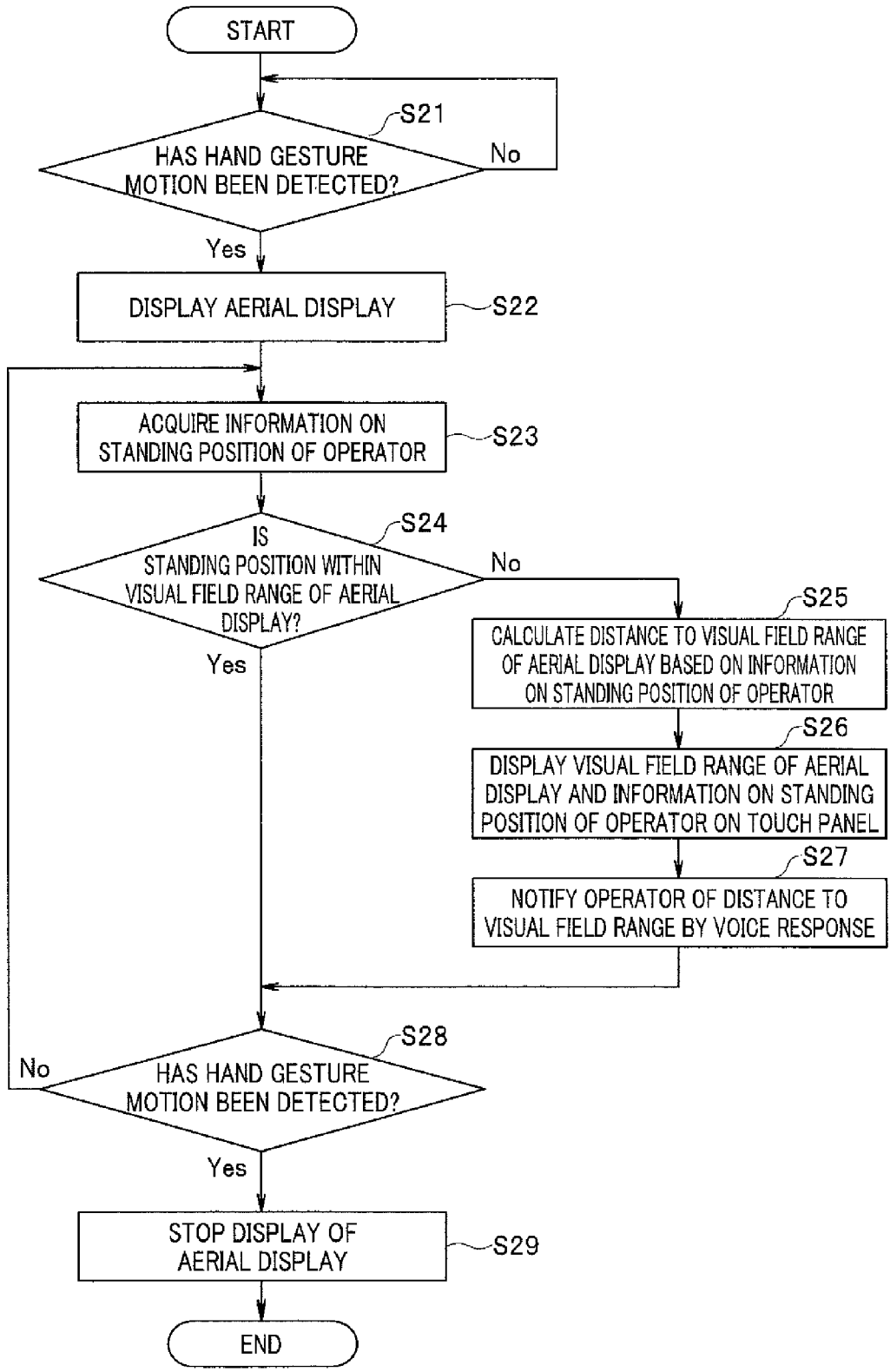
FIG. 8 is a flowchart showing a control action of an aerial display in the medical system according to the third embodiment.
Figure 9:
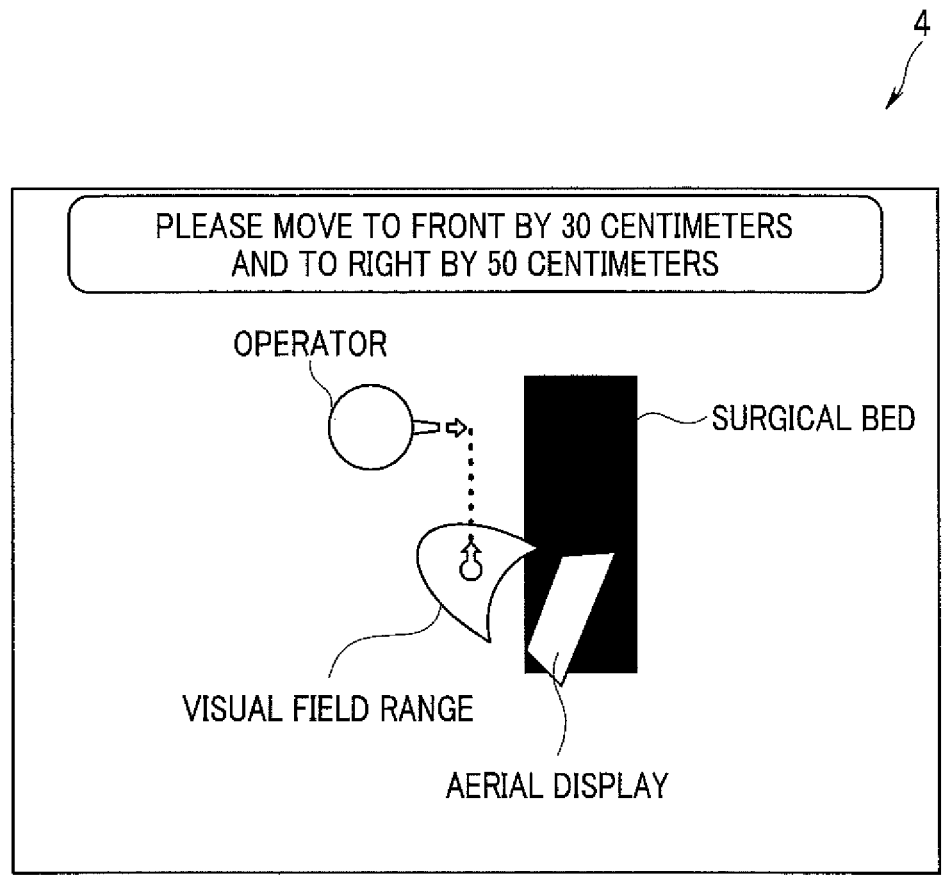
FIG. 9 illustrates one display example of an operation panel in the medical system according to the third embodiment.

FIG. 8 is a flowchart showing the control action of the aerial display in the medical system according to the third embodiment. Further, FIG. 9 illustrates one display example of the operation panel in the medical system according to the third embodiment.

As shown in FIG. 8, when the control section 131 in the system controller 103 detects the hand gesture motion of the operator 100 based on the information from the gesture sensor 114 (step S21), the control section 131 controls the display of the monitor for aerial display 111, to show the virtual aerial display 115 in the position which is plane-symmetrical to the display surface of the monitor for aerial display 111 with respect to the plate for aerial display 112 (step S22).

Then, the control section 131 acquires the information related to the standing position of the operator 100 in the surgery room (step S23), the information having been detected by the gesture sensor 114, and determines whether or not the current standing position of the operator 100 is within the visual field range of the virtual aerial display 115 (step S24).

As long as the standing position of the operator 100 is within the visual field range of the virtual aerial display 115 in the step S24, the control section 131 continues to show the virtual aerial display 115 until confirming that the operator 100 indicates his or her intention of stopping the showing of the virtual aerial display 115 again with the hand gesture motion (step S28).

When the standing position of the operator 100 is outside the visual field range of the virtual aerial display 115 in the step S24, or the operator 100 moves from the inside to the outside of the visual field range, the control section 131 acquires the information on the standing position of the operator 100 in the surgery room from the gesture sensor 114 and calculates the distance from the standing position of the operator 100 to the visual field range of the virtual aerial display 115 (step S25).

Next, the control section 131 in the system controller 103 performs control to display the information (for example, information and the like as shown in FIG. 9) indicating the positional relationship between the standing position of the operator 100 and the visual field range of the virtual aerial display 115 on the operation panel 4 (step S26).

Specifically, as shown in FIG. 9, for example, the information schematically displays the positional relationship among the operator 100, the visual field range of the virtual aerial display 115, and the virtual aerial display 115 itself, and provides the information (navigation information), which relates to the distance, direction, or the like from the current position to enter the visual field range of the virtual aerial display 115, to the operator 100. For example, when the determination section determines that the operator 100 is outside the visual field range of the virtual aerial display 115, the control section 131 causes a notice for guiding the operator 100 into the visual field range of the virtual aerial display 115 to be displayed on the display panel 5.

Furthermore, the control section 131 in the system controller 103 controls the speaker 42 to provide the information for guiding the operator 100 into the visual field range of the virtual aerial display 115, for example, the above-described navigation information to the operator 100 by voice response (step S27).

When the control section 131 confirms the hand gesture motion performed by the operator 100 again (that is, the motion based on the intention of the operator 100 to stop the showing of the virtual aerial display 115) in the step S28, the control section 131 stops the display of the image on the monitor for aerial display 111 and also stops the display of the virtual aerial display 115 (step S29).

As described above, the medical system according to the third embodiment enables the virtual aerial display provided with the input operation function (GUI function) like the touch panel to be shown in the accurate spatial position in the surgery room, similarly as in the first embodiment, and enables the surgeon who is in the sterilized area to operate various kinds of peripheral equipment in the medical system as if the surgeon operates the touch panel without touching the devices located in the unclean area.

In addition, the medical system according to the third embodiment is capable of accurately guiding the operator into the visual field range of the virtual aerial display, even if the medical system is a smaller-scale system in which the showing position of the virtual aerial display in the surgery room is restrictively limited, compared with the system in the above-described first embodiment.

In addition, since the medical system according to the third embodiment is the smaller-scale system compared with the system in the first embodiment, it is possible to show the virtual aerial display with lower cost than in the first embodiment.

Note that the plate for aerial display 112 is disposed at the cut-out part of the ceiling 116 and the monitor for aerial display 111 is disposed at the above-ceiling portion of the ceiling 116 in the third embodiment. The third embodiment, however, is not limited to such a configuration, and the same working effects can be provided even if the plate for aerial display 112 is disposed at a cut-out part of a predetermined wall surface in the surgery room and the monitor for aerial display 111 is disposed on the rear surface side portion of the wall.

Furthermore, in the first and second embodiments, the showing system of the virtual aerial display is activated with the "voice input" by the operator as a trigger. The first and second embodiments, however, are not limited to such a configuration, and the "hand gesture motion" of the operator may be a trigger for activating the showing system as disclosed in the third embodiment, instead of or in combination with the "voice input".

Conversely, in the third embodiment, the "voice input" may be a trigger for activating the showing system instead of or in combination with the "hand gesture motion".

Furthermore, the trigger for activating the showing system of the virtual aerial display in the above-described embodiments is not limited to the "voice input" or "hand gesture motion" of the surgeon as the operator, but may be other indication of intention by the surgeon, or operation and the like performed by a person other than the surgeon.

Each of the "sections" in the present specification is conceptual definition corresponding to each function in the embodiments and does not correspond to a specific hardware or a software routine one for one. Therefore, in the present specification, embodiments are described supposing the virtual circuit blocks (sections) having the respective functions in the embodiments.

In addition, the steps in the respective procedures in the embodiments may be executed by changing the execution order of the steps, by executing a plurality of steps at the same time, or may be executed in a different order for each execution of the steps unless contrary to the nature of the embodiment. Furthermore, all or a part of the steps in the respective procedures in the embodiments may be executed by a hardware.

Some embodiments of the present invention have been described, but these embodiments are described as examples and there is no intention to limit the range of the invention. These new embodiments can be executed in various forms and various kinds of omission, replacement and changes are possible without departing from the gist of the invention.

These embodiments and modifications thereof are included in the range and gist of the invention and in the range equivalent to that of the invention recited in claims.

The present invention is not limited to the above-described embodiments and various changes, modifications, and the like are possible without changing the gist of the invention.

The medical system according to the present invention is capable of providing a medical system that can show a virtual aerial display including an input operation function like a touch panel in an accurate spatial position in the surgery room.

What is claimed is:

1. A medical system that is capable of displaying a virtual image, comprising:
    a sensor comprising hardware, wherein the sensor implements:
        a first detection section that detects information related to at least one of a position and an orientation of an operator;
        a second detection section that detects a position of an object in a surgery room; and
    a processor comprising hardware, wherein the processor implements:
        a calculation section that calculates an area where the virtual image is to be arranged in the air based on the information;
        a determination section that determines whether or not the object is present in the area based on a result of the detection by the second detection section; and
        a control section that causes the virtual image to be arranged in the area based on a determination result by the determination section.

2. The medical system according to claim 1, wherein
    the second detection section detects the object present in the area, and
    the control section arranges the virtual image in the area when the determination section determines that the object is not present in the area.

3. The medical system according to claim 1, wherein the information includes at least one of a standing position of the operator, a position of a face of the operator and an orientation of the face of the operator.

4. The medical system according to claim 1, further comprising,
    a third detection section that detects positions of a hand and fingers of the operator,
    wherein the virtual image includes an operation screen, and
    the control section adjusts a position and an orientation of the virtual image such that the positions of the hand and the fingers match with the operation screen.

5. The medical system according to claim 4, wherein
    the determination section determines whether or not the operator is within a visual field range of the virtual image based on the information,
    the control section enables an operation on the operation screen when the determination section determines that the operator is within the visual field range of the virtual image, and
    the control section disables the operation on the operation screen when the determination section determines that the operator is outside the visual field range of the virtual image.

6. The medical system according to claim 5, further comprising,
    a display section that displays information related to a surgery,
    wherein the control section causes a notice for guiding the operator into the visual field range of the virtual image to be displayed on the display section, when the determination section determines that the operator is outside the visual field range of the virtual image.

7. The medical system according to claim 4, wherein the first detection section, the second detection section, and the third detection section acquire the information, the position of the object, and the positions of the hand and fingers, respectively, based on an output from a gesture sensor.

8. The medical system according to claim 1, further comprising,
    a monitor, and a plate for changing a traveling direction of a light beam,
    wherein the virtual image is displayed by image-forming the light beam emitted from the display surface of the monitor in a position symmetrical to a display surface of the monitor, with the plate as a plane of symmetry.

9. The medical system according to claim 8, further comprising,
    an arrangement section that arranges the monitor in a position so as to enable the virtual image to be displayed, based on an instruction from the control section.

10. The medical system according to claim 9, wherein the arrangement section supports the monitor from a ceiling or a wall in a room such that the monitor is movable.

* * * * *